United States Patent [19]

Costello et al.

[11] Patent Number: 5,399,718

[45] Date of Patent: Mar. 21, 1995

[54] DIRECT FLUORINATION PROCESS FOR MAKING PERFLUORINATED ORGANIC SUBSTANCES

[75] Inventors: Michael G. Costello; George G. I. Moore, both of Afton, Minn.

[73] Assignee: Minnesota Mining and Manufacturing Company, St. Paul, Minn.

[21] Appl. No.: 187,123

[22] Filed: Feb. 1, 1994

Related U.S. Application Data

[60] Continuation of Ser. No. 612,306, Nov. 13, 1990, abandoned, which is a division of Ser. No. 278,965, Dec. 2, 1988, abandoned.

[51] Int. Cl.$^6$ .................. C07C 53/21; C07C 69/63
[52] U.S. Cl. .................. 549/266; 554/226; 560/180; 560/184; 560/192; 560/227
[58] Field of Search ............. 560/180, 184, 192, 227; 554/226; 549/266

[56] References Cited

U.S. PATENT DOCUMENTS

| | | | |
|---|---|---|---|
| 2,713,593 | 7/1955 | Brice et al. | 260/535 |
| 3,847,978 | 11/1974 | Sianesi et al. | 562/577 |
| 4,089,869 | 5/1978 | Yamabe et al. | 549/273 |
| 4,523,039 | 6/1985 | Lagow | 568/615 |
| 4,686,024 | 8/1987 | Scherer | 549/347 |
| 4,755,567 | 6/1988 | Bierschenk | 549/504 |
| 5,093,432 | 3/1992 | Bierschenk | 525/331 |

FOREIGN PATENT DOCUMENTS 15760 9/1966 Japan.

OTHER PUBLICATIONS

Adcock et al., J. Am. Chem. Soc., 103, 6937 (1981).

*Primary Examiner*—José G. Dees
*Assistant Examiner*—Joseph M. Conrad
*Attorney, Agent, or Firm*—Gary L. Griswold; Walter N. Kirn; Lucy C. Weiss

[57] ABSTRACT

A liquid phase process for making perfluorinated organic substances which comprises directly contacting in a temperature-controlled reactor a diluted solution or dispersion of a perfluorinateable, organic substance in a liquid, inert medium with a stoichiometric excess of fluorine gas, optionally diluted with an inert gas, to perfluorinate said organic substance at a temperature and a flow rate of inert gas (if used) sufficient to volatilize the resulting by-product hydrogen fluoride, removing said hydrogen fluoride from the reactor as it is produced, and separately removing from the reactor the resultant solution or dispersion of perfluorinated organic substance.

10 Claims, No Drawings

DIRECT FLUORINATION PROCESS FOR MAKING PERFLUORINATED ORGANIC SUBSTANCES

This is a continuation of application No. 07/612,306, filed Nov. 13, 1990, which is a division of application No. 07/278,965, filed Dec. 2, 1988, both now abandoned.

This invention relates to perfluorinated organic substances and to a process for making them by the direct fluorination of their perfluorinateable precursors, such as ethers, alcohols, carboxylic acid esters, acid fluorides, sulfonyl fluorides, and sulfonate esters.

Prior to some relatively recent advances in direct fluorination, it was generally accepted that the highly exothermic reaction of fluorine, $F_2$, with organic compounds is accompanied by quick evolution of heat and by one or more of such phenomena as carbon-carbon scission or fragmentation, polymer formation, ignition, combustion, and violent explosions, the heat removal being the main problem in direct fluorination—see, for example, U.S. Pat. No. 4,523,039 (Lagow et al.) and Kirk-Othmer "Encyclopedia of Chemical Technology", 3rd Ed., Vol. 10, pages 636, 840–855, John Wiley & Sons, Inc., New York (1980).

Various diverse fluorination methods or techniques which have been proposed to overcome problems in direct fluorination are dilution of the fluorine with an inert gas, use of low temperatures, use of inert solvents to dissipate heat, use of partially-fluorinated starting materials, dilution of the organic feed, use of hydrogen fluoride scavengers, and combinations of these techniques, such as that described by Adcock et al., *J. Am. Chem. Soc.*, 103, 6937 (1981). In the process of Adcock et al., the organic is vaporized and condensed into aggregates around sodium fluoride aerosol particles at low temperatures (initially −65° C.) in carrying out the fluorination, but the yields of fluorinated product, e.g. tetraethylene glycol dimethyl ether, are relatively low.

U.S. Pat. No. 4,755,567 (Bierschenk et al.) discloses a recent improvement, viz., the direct fluorination of hydrocarbon ether, such as polyethylene oxide and polydioxolane, at temperatures, for example, of 30° to 40° C., in the presence of hydrogen fluoride scavengers such as sodium fluoride. Although this fluorination technique of Bierschenk et al. results in significant yields of perfluorinated product, that product contains fractions with lower molecular weights than anticipated, due to fragmentations.

Another fluorination process is described in European Patent Application 0077114 (the Green Cross Corp.), published Apr. 20, 1983, in which the fluorination is carried out in an inert liquid medium, such as a perfluorochemical, with undiluted fluorine in stoichiometric excess, the relatively good or high yields of perfluorinated product apparently requiring use of a partially-fluorinated precursor and preferably requiring ultraviolet light.

U.S. Pat. No. 4,686,024 (Scherer et al.) discloses the liquid phase photofluorination of partially-fluorinated or non-fluorinated compounds with diluted or undiluted fluorine in perfluorohexane, 1,1,2-trichloro-1,2,2-trifluoroethane, or a mixture thereof as a reaction medium in which the starting material is soluble.

European Patent Application 0269029 (Ausimont S.p.A.), published Jun. 1, 1988, also describes a liquid phase process for preparing perfluoroethers. The process involves the direct reaction of elemental fluorine, which is diluted with an inert gas, with an "hydrogenated ether compound" in the presence of a perfluoropolyether compound and an alkali metal fluoride. High yields of thoroughly fluorinated compounds are achieved, but the method requires the use of the alkali metal fluoride as a hydrogen fluoride scavenger.

Briefly, this invention, in one aspect, provides an improved liquid phase process of direct fluorination of perfluorinateable organic substance, such as ethers, alcohols, carboxylic acid esters, acid fluorides, sulfonyl fluorides, and sulfonate esters as starting material, wherein the fluorination is substantially carried out in the absence of any significant amount of hydrogen fluoride. The process comprises directly contacting a diluted solution or dispersion of said organic substance in a normally liquid, inert medium with a stoichiometric excess of fluorine gas, $F_2$, preferably diluted with an inert gas such as nitrogen, in a temperature-controlled reactor to perfluorinate said organic substance at a temperature and a flow rate of inert gas (if used) sufficient to volatilize by-product hydrogen fluoride, HF, removing said hydrogen fluoride from the reactor as it is produced (and not recycling it) so that the fluorination is substantially carried out in a hydrogen fluoride-free environment, and separately removing from the reactor the resultant solution or dispersion of perfluorinated organic substance. The fluorine gas is preferably diluted with the inert gas in order to better control the fluorination reaction and to enhance removal of the by-product hydrogen fluoride from the reactor. The perfluorinated organic substance can be separated from the inert medium, e.g. by distillation, to obtain the perfluorinated organic substance as the product of the process. Alternatively, the solution or dispersion of this perfluorinated organic substance can be treated with a reagent or reactant, depending on the nature of the perfluorinated organic substance, and the perfluorinated organic substance then separated from the inert medium.

Each of the perfluorinated organic substances resulting from the process, some of which substances are novel aspects of this invention, comprises, consists, or consists essentially of one or more perfluoro compounds, oligomers, or polymers. Such perfluoro materials can have one or more chlorine atoms, e.g. one chlorine atom per 3 carbon atoms or as many as 2, 3, or more chlorine atoms per 6 to 30 or more carbon atoms, and are otherwise essentially fully-fluorinated, i.e., perfluorinated, with residual carbon-bonded hydrogen content of generally less than about 0.4 mg/g and preferably less than about 0.1 mg/g, e.g. 0.01 to 0.05 mg/g. The perfluoro organic substances can be perfluoroethers, perfluoroacyl fluorides, perfluorocarboxylic acid esters, perfluorosulfonyl fluorides, and perfluorosulfonates, species in each of these classes being known materials of known utility.

The direct fluorination process of this invention—notwithstanding that it does not require the use of very low reaction temperatures or partially-fluorinated starting material and is carried out in the absence of hydrogen fluoride scavengers, e.g. NaF, and UV illumination—can be carried out to produce high yields of perfluorinated product, the amount of undesired cleavage or polymerized or rearranged products, if any, being significantly low or exceedingly minor in amount. Starting materials which can be used include those, such as ethers, which heretofore were believed too reactive with HF or too fragile to withstand direct fluorination at the temperatures employed in the process of this invention in the absence of hydrogen fluoride scavenger. In addition to providing high yields, the process of this invention can be carried out in greatly simplified process equipment and has increased volume efficiency compared with prior art processes employing solid hydrogen fluoride scavenger, the use of which entails various processing and operating disadvantages, such as solids handling problems, regeneration of the scavenger, and through-put limitations.

The fluorination process of the invention can be carried out in a "batch" manner, whereby the reactor is charged with a batch of the perfluorinateable organic substance (either neat or dissolved or dispersed in an inert, halogenated liquid or a fluorine-reactive liquid) and the inert liquid reaction medium to provide a very dilute concentration of the starting material, e.g. up to about 10% by weight, and then the fluorine gas (preferably diluted with inert carrier gas) is continuously bubbled through the solution or dispersion of the starting material, by-product hydrogen fluoride being continuously removed from the reactor as a gas (along with the unreacted fluorine gas), which removal is preferably aided by the flow of inert carrier gas through the reactor. After fluorination is complete, the reaction product is removed from the reactor.

Alternatively, the fluorination can be carried out in a "semi-continuous" manner, with the starting material (either neat or dissolved or dispersed in a liquid, such as an inert halogenated liquid or a fluorine-reactive liquid) continuously pumped or otherwise fed as a gas, liquid, or solid into the reactor containing inert liquid reaction medium, e.g., at a rate of about 1 to 3 g/hr into 400 mL of inert liquid, as the fluorine gas (preferably diluted with inert gas) is bubbled through, e.g., at a fluorine flow rate of about 40 to 120 mL/min and an inert gas flow rate of about 150 to 600 mL/min., by-product hydrogen fluoride and unreacted fluorine being continuously removed from the reactor, which removal is preferably aided by the inert carrier gas. After fluorination is complete, the reaction product is removed from the reactor.

The fluorination can also be carried out in a "continuous" manner, with the starting material (either neat or dissolved or dispersed in an inert halogenated liquid or a fluorine-reactive liquid) continuously fed into the reactor containing inert liquid reaction medium, as described above, as the fluorine gas (preferably diluted with inert gas) is bubbled through the liquid reaction mixture. The solution or dispersion of unreacted and reacted starting material and the stream of unreacted fluorine, hydrogen fluoride gas, and inert carrier gas are continuously removed from the reactor and the necessary separations can be made to recover the perfluorinated product and, if desired, the unreacted fluorine and unreacted starting material recycled. The amount of inert liquid medium in the reactor can be maintained at a constant level by addition of recycled or fresh liquid.

In general, the continuous addition of starting material is preferred and provides a higher yield, better product quality, and more efficient use of fluorine, though the batch mode has similar advantages if the "polishing" finishing step (described below) is used.

Suitable liquids for use as inert reaction media in the process of the invention are those which can function as solvents or dispersants for the starting material and which do not react appreciably with diluted fluorine, that is, media which are relatively inert to fluorine, at the temperatures utilized. The concentration of the starting material in the inert reaction medium is relatively low so as to more easily control the reaction temperature. Examples of liquids useful as such reaction media include perfluoroalkanes such as perfluorinated pentanes, hexanes, heptanes, octanes, and decalins, perfluoroethers such as Fluorinert TM FC-75, Krytox TM, and Fomblin TM, perfluorotrialkylamines such as Fluorinert TM FC-40, chlorofluorocarbons such as Freon TM 113, 1,1,2-trichlorotrifluoroethane, and Freon TM 11, fluorotrichloromethane, chlorofluoroethers such as 2,5,5-trichloroperfluoro-2-butyl tetrahydrofuran, perfluoro-bis(chloroethyl)ether, and perfluoropolyepichlorohydrin, perfluoroalkanesulfonyl fluorides such as perfluoro-1,4-butanedisulfonyl fluoride and perfluorobutanesulfonyl fluoride, and mixtures thereof. These inert media are conveniently used at atmospheric pressure. Lower molecular weight members of the above classes can also be used, but elevated pressures are then required to provide a liquid phase. In some cases it may be feasible to use the perfluorinated product as a reaction medium, use of which may render unnecessary the separation of perfluorinated product from reaction medium. Liquids suitable for use in diluting the starting material (prior to its addition to the inert liquid reaction medium) include the inert liquids described above as well as liquids which may to some degree react with dilute fluorine such as, for example, carbon tetrachloride, chloroform, and fluorinated alkanes containing one or two hydrogens, or materials which contain little or no halogen but in themselves are perfluorinateable to useful products.

The reactor used in the process of this invention can be equipped with a cooling jacket or internal cooling coils to control the temperature, a stirrer to vigorously agitate the reaction mixture as the fluorine gas is bubbled through it, and, if volatilized reaction medium and/or low boiling perfluorinated product are to be recovered, a reflux condenser. Generally, the reactor temperature will be maintained at a temperature in the range of about 0° C. to about +150° C., preferably about 0° C. to about 50° C., most preferably about 10° C. to 30° C., sufficient to volatilize the hydrogen fluoride by-product and with the aid of the flowing inert gas cause the purging of the by-product from the fluorination reactor as it is generated. The design and temperature of the condenser should be such as to minimize or prevent the hydrogen fluoride from returning to the reactor, e.g., either by selective condensation of the inert liquid reaction medium and other organic substances, allowing the hydrogen fluoride to pass through the condenser, or by total condensation into a separate vessel of hydrogen fluoride, inert liquid reaction medium, and other organic substances followed by separation of the hydrogen fluoride as the upper liquid phase and, if desired, recycle of the lower liquid phase. The minimization or prevention of the return of hydrogen fluoride is of particular significance in the case of starting materials such as ethers and olefinic material, which are adversely affected by hydrogen fluoride, a low yield of the corresponding perfluoro product generally resulting if the hydrogen fluoride is retained in the reactor during fluorination. The inert carrier gas flow rate sufficient for effective removal of hydrogen fluoride varies according to reactor and condenser geometry. However, we have observed that a rate of about 1300 mL/min of 20% fluorine in nitrogen in a reactor containing 2 liters of Freon TM 113 at 20° C. connected to a condenser consisting of about 6 meters of coiled 1.27 cm diameter stainless steel tubing at −25° C. gives high yields of perfluorinated ether product. Fluorine is preferably used at a concentration of about 5 to 50 volume %, more preferably about 10 to 25 volume %, in an inert gas such as, for example, nitrogen, argon, helium, $CF_4$, or $SF_6$, preferably nitrogen, and is maintained in stoichiometric excess throughout the fluorination, for example, at an excess of up to about 15 to 40% or higher. Pure fluorine can also be used but is not preferred, due to considerations of both safety and economy.

Although the semi-continuous and continuous processes of this invention yield perfluorinated product which may contain small amounts of fluorinated material having one or a few residual hydrogen atoms, the product is essentially fully fluorinated, i.e., perfluorinated, with a residual hydrogen content of less than about 0.4 mg/g and generally less than about 0.1 mg/g. The batch process, however, gives product with a somewhat higher residual hydrogen content, e.g., about 7 mg/g. The liquid reaction product can be distilled to remove the inert liquid reaction medium and any low-boiling by-products, and any residual hydrogen content and traces of undesired carboxylic acid derivatives can be essentially completely removed upon treating the distillate at elevated temperature, for example, at 150° C. or higher, with fluorine, preferably diluted with an inert gas such as nitrogen, to, in a sense, "polish" the product, the resulting hydrogen fluoride and any carbonyl fluorides being removed along with the unreacted fluorine gas used in this polishing technique. (This polishing technique cannot be effectively utilized if the desired end product is a perfluorinated carboxylic acid.) Alternatively, non-functional perfluorinated product can be purified by treatment with a base, such as potassium hydroxide. Perfluorinated acids can be purified by treatment with a base, followed by acidification and distillation.

The organic substances which can be used as starting materials are those which are "perfluorinateable," that is, those which contain carbon-bonded hydrogen atoms which are replaceable by fluorine and can contain carbon-carbon unsaturation which is saturateable with fluorine. Representative examples of organic substances which can be perfluorinated by the process of this invention include monoethers, such as dioctyl ether, glymes, such as heptaethylene glycol dimethyl ether, polyethers, such as polyepichlorohydrin and polyethylene glycol, alcohols, such as octanol and butoxyethoxyethanol, acetals, such as polydioxolane, polytrioxocane, polymethyleneoxide, polybutyrylaldehyde, bis(2-butoxyethoxy)methane, 3,6,9,11-tetraoxaheptadecane, 5,7,10,13-tetraoxaheptadecane, 2,14-dimethyl-4,7,9,12-tetraoxapentadecane, 3,6,9,11,14,17-hexaoxanonadecane, 2,5,7,10,13,16,18,21-octaoxadocosane, 3,6,8,11,14,16,19-heptaoxaheneicosane, and 3,5,8,11,14-pentaoxaoctadecane, carboxylic acid esters, such as 2-methylbutyl acetate, dimethyl adipate, caprolactone, methyl caprylate, n-octyl acetate, n-octadecyl acetate, methyl benzoate, polyethylene glycol bis(trifluoroacetate), tetraethylene glycol diacetate and 2-(2-ethoxy)ethoxyethyl acetate, and polyethylene glycol monoethylether monoacetate, sulfonyl fluorides, such as octanesulfonyl fluoride, acid fluorides, such as octanoyl fluoride, and benzoyl fluoride, and sulfonate esters such as methyl octanesulfonate.

Novel perfluorinated organic substances prepared by the process of this invention include: perfluoro(2-ethoxy-2-ethoxyethyl acetate), perfluoro(tetraethylene glycol diacetate), dimethyl perfluoro-3,6,9-trioxaundecane-1,11-dioate, perfluoro(polyethylene glycol monomethyl ether monoacetate), methyl perfluoromethoxypoly(ethyleneoxy) acetate, perfluoro(polyethylene glycol diacetate), dimethyl ester of perfluoro(alpha, omega-bis-carboxylmethyl ether of polyethylene glycol), perfluoro(methyl caprylate), perfluoro(octyl acetate), perfluoro(octadecyl acetate), perfluoro(n-octadeconoic acid), perfluoro(dimethyl adipate), perfluoro(methyl-3-n-pentyloxypropionate), methyl perfluoro-3-n-pentyloxypropionate), and perfluorocaprolactone.

The perfluorinated ethers prepared by the process of this invention are inert fluids useful as hydraulic fluids, heat transfer fluids, pump fluids for corrosive environments, and fluids for vapor phase condensation heating for soldering and polymer curing applications. The perfluorinated carboxylic acid derivatives and sulfonic acid derivatives are useful, for example, as precursors to fluoroalcohol acrylates, for chemical or physical incorporation into or treatment of hydrocarbon materials to impart fluorochemical properties thereto, and they may be converted to acids which are, as well as their salts, useful as surface active agents. The perfluorinated ether acids are useful for conversion to inert perfluorinated ether fluids.

This invention is further illustrated by the following examples, but the particular materials and amounts thereof recited in these examples, as well as other conditions and details, should not be construed to unduly limit this invention.

EXAMPLES

Example 1

A 2-liter, jacketed vessel of Monel TM metal was equipped with a magnetic drive agitator, gas feed line, organic reactant feed line, and a reflux condenser. The gas feed line was a 0.3 cm diameter tube reaching to a point below the bottom impeller of the agitator. The organic reactant feed line was a 0.15 cm diameter tube connected to a syringe pump. The reflux condenser consisted of about 6 m of two coiled concentric tubes, the inner tube having a 1.27 cm diameter and the outer tubing having a 2.54 cm diameter. Gases from the reactor were cooled in the inner tube by refrigerant, ethylene glycol-water, flowing in the annulus between the two tubes. The reactor was charged with 1.8 liters of Freon 113 and purged with 650 mL/min of nitrogen for 20 min. The gas stream was changed to a mixture of 160 mL/min fluorine and 650 mL/min nitrogen. Afer 12 min, injection of a 250 mL mixture of 57.7 g (0.23 mol) bis(butoxyethoxy)methane and Freon 113 at 12 mL/hr was begun. The reactor contents were maintained at about 19°–20° C. throughout the reaction. The condenser temperature was about −22° C. The fluorine flow was continued 10 min after the organic feed was finished. The reactor was then purged with nitrogen for one hr. The reactor contents were removed and distilled under vacuum at 30° C. The residue was 155.9 g, shown by gas chromatographic analysis (GC) to be 86.7% pure perfluoro-bis(2-butoxyethoxy)methane. H-nmr analysis of a similar run showed 0.07 mg/g residual hydrogen atoms.

Example 2

A reactor essentially the same described above but fitted with a different condenser, viz., a 1-meter long assemblage of three concentric tubes with ethylene glycol-water refrigerant flowing in the center tube and the outer annulus of the asemblage and with reactor effluent flowing through the inner annulus via an inlet tube depending therein and thence exiting via an outlet in the upper end of the inner annulus. The reactor was charged with 2 liters of Fluorinert FC-72 and purged with 610 mL/min nitrogen for 10 min. The gas stream was changed to a mixture of 164 mL/min fluorine and 610 mL/min nitrogen. After 15 min, injection of 60.0 g bis(2-butoxyethoxy)methane at 3.09 mL/hr was begun. The reactor temperature was maintained at about 18°-20° C. and the condenser at about −26° C. The fluorine flow was continued for approximately 10 min after the addition of the organic reagent was completed. The reactor was purged with nitrogen for one hour and the reactor contents were removed. Distillation on a 3-plate Snyder column produced a yield of 58% of perfluoro-bis(2-butoxyethoxy)methane.

Example 3

In the same manner as Example 2, 97.2 g of bis(2-butoxyethoxy)methane was fluorinated over a 20 hr. period at about 70° C. in Fluorinert FC-75, giving perfluoro-bis(2-butoxyethoxy)methane in 55% yield.

Example 4

In the same manner as Example 2, Fluorinert FC-87 was used as the reaction medium, producing perfluoro-bis(2-butoxyethoxy)methane in 42% yield.

Example 5

The same reactor described above in Example 1 was charged with 2 liters of Freon 113 and purged with 1000 mL/min nitrogen for 20 min. The gas stream was changed to a mixture of 325 mL/min fluorine and 1000 mL/min nitrogen. After 5 min, injection of a 200 mL mixture of 154.7 g (0.88 mol) 2-ethoxy-2-ethoxyethyl acetate and Freon 113 at 10 mL/hr was begun. The reactor temperature was maintained at about 20° C. throughout the run; the condenser was at about −22° C. The fluorine flow was continued approximately 10 min after the organic feed was finished. The reactor was purged with nitrogen for 3 hr, and the reactor contents, a solution of predominantly perfluoro(2-ethoxy-2-ethoxyethyl acetate) in Freon 113, were removed and mixed with 100 mL methanol containing 10 mL 14% boron trifluoride in methanol. This mixture was washed with water, and the lower layer was dried over $MgSO_4$. Distillation on a 3-plate Snyder column afforded 214.9 g (69%) of methyl perfluoro(ethoxyethoxyacetate), bp 110°-20° C. A similar run at −6° C. in the presence of 156 g NaF gave 152.0 g (48%).

Example 6

A 600 mL aluminum reactor was equipped with a stirrer, a 0.6 cm fluorine feed tube, a 0.15 cm organic feed tube, and a 50 cm long straight double-tube condenser, the inner tube having a diameter of about 1.27 cm and the outer tube having a diameter of about 2.54 cm, with ethylene glycol-water refrigerant flowing in the annulus between the two tubes. The reactor was charged with 400 mL Freon 113 and purged with nitrogen. A mixture of 46.5 mL/min fluorine and 170 mL/min nitrogen was introduced into the liquid. Then, a 200 ml mixture of 27.8 g (0.1 mol) tetraethyleneglycol diacetate in Freon 113 was injected into the liquid at 9.2 mL/min. The reactor temperature was maintained at about 22° C. and the condenser temperature at about −17° C. After the addition of organic reactant was completed, the fluorine flow was discontinued and the reactor contents—a solution of predominantly perfluoro(tetraethylene glycol diacetate) in Freon 113— were worked up as above in Example 5 with methanolic boron trifluoride. The Freon 113 was stripped off, leaving 28.0 g (60%) crude product. GC analysis showed 73.7% of dimethyl perfluoro-3,6,9-trioxaundecane-1,11-dioate and 5.4% of methyl perfluoro-3,6,9-trioxadecanoate. Very similar results were observed at −6° C. in the presence of NaF.

Example 7

In the same manner as Example 1, 150 g Carbowax TM 550 acetate (made from Carbowax 550 polyethylene glycol monomethyl ether and excess acetyl chloride) was fluorinated at about 20° C. and the product, perfluoro(polyethylene glycol monomethyl ether monoacetate), was washed with methanolic boron trifluoride to give 164 g (45%) of crude product which was principally a mixture of methyl perfluoromethoxypoly(ethylene oxy) acetates, $CF_3O(C_2F_4O)_nCF_2CO_2CH_3$, where n is about 8 to 13.

Example 8

In the same manner as Example 1, 320 g of PEG TM 600 polyethylene glycol diacetate (made from PEG 600 polyethylene glycol and excess acetyl chloride) was fluorinated and the crude product, perfluoro(polyethylene glycol diacetate), was worked up as in Example 5. The worked-up product was principally a mixture of the dimethyl esters of perfluoro(alpha, omega-bis-carboxylmethyl ether of the polyethylene glycol) $CH_3O_2CCF_2O(CF_2CF_2O)_nCF_2CO_2CH_3$, when n is about 9 to 14 in admixture with a minor amount of $CF_3O(CF_2CF_2O)_nCF_2COOCH_3$, where n is about less than 14.

Example 9

In the same manner as Example 5, n-octadecyl acetate (made from octadecyl alcohol and acetyl chloride) was fluorinated at about 23° C. The resulting solution of perfluoro(n-octadecyl acetate) was washed with water to give 5.5 g perfluoro(n-octadecanoic acid), subsequently recrystallized from Fluorinert FC-75 to amp of about 155° C.

Example 10

In the same manner as Example 5, dimethyl adipate was fluorinated at about 23° C. and the product, a mixture of predominantly perfluoro(dimethyl adipate), was treated with methanol. Analysis by GC showed the main product to be dimethyl perfluoroadipate, with lesser amounts of methyl perfluorovalerate and hydrido-derivatives of the diester.

Example 11

In the same manner as Example 5, 26.1 g of bis(n-butoxyethoxy)ethane (made from n-butoxyethanol and acetaldehyde) was fluorinated. The product was distilled at 73°-90° C./15 Torr to a mixture of 70% perfluorobis(n-butoxyethoxy)ethane and 30% perfluorobutoxyacetic acid, as determined by F-nmr. The latter was removed by washing with base to give pure perfluoro-bis(n-butoxyethoxy)ethane, bp 180° C.

Example 12

In the same manner as Example 5, 24.7 g n-octanesulfonyl fluoride was fluorinated and the product was concentrated on a rotary evaporator at 30° C. to give 45.5 g of a mixture of equal parts perfluoro-n-octanesulfonyl fluoride and perfluoro-n-octane.

Example 13

In the same manner as Example 1, 91 g polyepichlorohydrin ($M_n$ 1500) was fluorinated to give the perfluorinated analog as a colorless oil, 142 g.

Example 14

In the same manner as Example 1, 151 g methyl 3-n-pentyloxypropionate (made by addition of n-pentanol to acrylonitrile and subsequent treatment with methanolic HCl) was fluorinated and the product, perfluoro(methyl 3-n-pentyloxypropionate), was treated with methanol, giving 209 g (79%) methyl perfluoro-3-n-pentyloxypropionate.

Example 15

In the same manner as Example 5, 30.0 g caprolactone was fluorinated and the product, perfluorocaprolactone, was treated with methanol to give 50.6 g of a mixture similar in composition to that of Example 10, with 44% by GC being dimethyl perfluoroadipate.

Example 16

The reactor system described in Example 2 was charged with 2 liters of Freon-113, 35.2 g PEG 8000 polyethylene glycol and purged with nitrogen for 20 min. A mixture of 500 mL/min nitrogen and 103 mL fluorine was introduced into the liquid. The reactor temperature was maintained at about 17°-18° C. and the condenser temperature at about −25° C. After 16.3 hours the fluorine flow was discontinued and the reactor contents were filtered to give 32.2 g solid fluorinated material. The liquid filtrate was distilled under vacuum at 30° C. to produce 13.2 g colorless fluorinated oil as residue.

Example 17

In the same manner as Example 5, 24.3 g n-2-butoxyethoxyethanol was fluorinated and the resulting product was worked up to give 10.0 g crude product, predominantly methyl perfluoro-2-butoxyethoxyacetate.

Various modifications and alterations of this invention will become apparent to those skilled in the art without departing from the scope and spirit of this invention.

What is claimed is:
1. Perfluoro(2-ethoxy-2-ethoxyethyl acetate).
2. Perfluoro(tetraethylene glycol diacetate).
3. Perfluoro(polyethylene glycol monomethyl ether monoacetate).
4. Methyl perfluoromethoxypoly(ethyleneoxy) acetate.
5. Perfluoro(polyethylene glycol diacetate).
6. Dimethyl ester of perfluoro(alpha, omega-bis-carboxylmethyl ether of polyethylene glycol).
7. Perfluoro(methyl caprylate).
8. Perfluoro(octyl acetate).
9. Perfluoro(ocetadecyl acetate).
10. Perfluoro(methyl-3-n-pentyloxypropionate).

* * * * *

UNITED STATES PATENT AND TRADEMARK OFFICE
CERTIFICATE OF CORRECTION

PATENT NO. : 5,399,718
DATED : March 21, 1995
INVENTOR(S) : Michael G. Costello and George G. I. Moore It is certified that error appears in the above-indentified patent and that said Letters Patent is hereby corrected as shown below:

Col. 8, line 49, delete "5.5 g" and insert --45.5 g --.

Col. 8, line 50, delete "amp" and insert -- a mp --.

Signed and Sealed this

Thirtieth Day of April, 1996

Attest:

BRUCE LEHMAN

Attesting Officer  Commissioner of Patents and Trademarks